United States Patent [19]

Pages et al.

[11] Patent Number: 5,637,082

[45] Date of Patent: Jun. 10, 1997

[54] ADAPTIVE APHERESIS APPARATUS

[75] Inventors: Etienne Pages, Saint Avertin, France; Stephen Bernt, Dover; Stephen Viviano, Mansfield, both of Mass.

[73] Assignee: Haemonetics Corporation, Braintree, Mass.

[21] Appl. No.: 604,864

[22] Filed: Feb. 22, 1996

[51] Int. Cl.⁶ .................................................. A61M 37/00
[52] U.S. Cl. .................................................. 604/6
[58] Field of Search ................. 604/4, 5, 6; 210/645, 210/647, 782

[56] References Cited

U.S. PATENT DOCUMENTS

| | | |
|---|---|---|
| 3,489,145 | 1/1970 | Judson et al. . |
| 3,737,096 | 6/1973 | Jones et al. . |
| 4,086,924 | 5/1978 | Latham, Jr. . |
| 4,185,629 | 1/1980 | Cullis et al. ..................... 604/6 |
| 4,197,847 | 4/1980 | Djerassi . |
| 4,464,167 | 8/1984 | Schoendorfer et al. . |
| 4,680,025 | 7/1987 | Kruger et al. . |
| 4,828,543 | 5/1989 | Weiss et al. ..................... 604/6 |
| 4,850,995 | 7/1989 | Tie et al. . |
| 4,968,295 | 11/1990 | Neumann ......................... 604/6 |
| 5,112,298 | 5/1992 | Prince et al. ..................... 604/6 |
| 5,135,667 | 8/1992 | Schoendorfer . |
| 5,385,539 | 1/1995 | Maynard . |
| 5,387,187 | 2/1995 | Fell et al. . |
| 5,496,265 | 3/1996 | Langley et al. ..................... 604/5 |
| 5,505,685 | 4/1996 | Antwiler ......................... 604/6 |

FOREIGN PATENT DOCUMENTS

| | | |
|---|---|---|
| 0128683 | 12/1984 | European Pat. Off. . |
| 0171749 | 8/1985 | European Pat. Off. . |
| 9000059 | 1/1990 | WIPO . |

OTHER PUBLICATIONS

Fr. M. de Wit, J.J. et al., Leucoytes: *Separation, Collection and Transfusion*, pp. 46–58.
Sadoff, B.J. et al., *Transfusion* 32(2):131–133 (1992).
Elias, M.K. et al., *Ann Hematol*:63:302–306 (1991).
De Graan–Hentzen, Y.C.E., *Transfusion* 29(9):757–760 (1989).
Steneker, I. et al., *Transfusion* 31(1):40–46.
Angelbeck, J.H., "An Overview of Pall Leukocyte Removal Filter Applications and the Sterile Docking Device" presented at 3rd International Congress World Apheresis Association, Apr. 9, 1990, Amsterdam, The Netherlands.
Pall Biomedical Products Corporation products brochure, "Pall PL100 Leukocyte Removal Filter for Platelet Transfusion".
Taborski, U. et al., *Beitr. Infusionther. Basel, Karger* 26:273–276 (1990).
Matthes, G. et al., *J. of Clin Apheresis* 9:183–188 (1994).

*Primary Examiner*—John G. Weiss
*Assistant Examiner*—Ki Young O
*Attorney, Agent, or Firm*—Cesari and McKenna

[57] ABSTRACT

Automated apheresis apparatus and methods avoid unneeded collection and return of blood components. An operator "dials in" a desired amount of one or more blood components, whereupon the invention calculates the number of cycles necessary to achieve the target and directly implements an appropriate apheresis procedure. The invention may vary the volume of the separation chamber instead of, or in addition to, modifying the number of collection cycles in order to reach a target collection point. The invention may utilize a return procedure whereby, prior to the final collection cycle, only a portion of the contents of the separation chamber is returned to the donor; the returned portion is calculated such that filling the partly empty separation chamber on the last collection cycle results in just meeting the collection target. The invention may also monitor, in real-time, the amount of desired product actually collected during an apheresis cycle, and based thereon calculate the number of cycles necessary to reach the target level. Finally, the invention may continuously compare overall blood collection volumes with the volume of blood product actually obtained in order to compute (or verify) a machine collection efficiency for each type of blood product collected.

18 Claims, 5 Drawing Sheets

ADAPTIVE APHERESIS APPARATUS

FIELD OF THE INVENTION

This invention relates to medical equipment, and in particular to apparatus for separating whole blood into components for collection.

BACKGROUND OF THE INVENTION

Whole human blood includes predominantly three types of specialized cells: red blood cells, white blood cells, and platelets. These cells are suspended in a complex aqueous solution of proteins and other chemicals called plasma. Although in the past blood transfusions have used whole blood, the current trend is to transfuse only those blood components required by a particular patient. This approach preserves the available blood supply and in many cases is better for the patient, since the patient is not exposed to unneeded blood components. Storage lifetimes can also be increased by packaging the individual blood products separately.

The blood components needed for the transfusion are taken from a donor by a process called apheresis in which the desired one, or more, specific components of the whole blood are separated and harvested by a blood-processing machine. The remaining components are returned to the donor. (As used herein, the term "donor" connotes anyone from whom blood is drawn for collection or processing, and can include volunteer donors or medical patients to whom blood collected components are returned.)

Using current methods, while only 10–12 minutes are required for a donor to donate whole blood, 30 minutes or longer may be necessary for donation of plasma or platelets by means of apheresis. As a result, the population willing to donate through apheresis is much smaller than the whole-blood donation population. This has become problematic as the need for plasma and platelets has greatly increased.

U.S. Pat. No. 5,387,187 discloses an apheresis method and apparatus that facilitates obtaining, from a single donor, standard units of blood components with hematocrit in the 65–70% range, and which is also capable of collecting volumes of plasma (with or without platelets) in the range of 400 ml in 20 minutes or less. The device provides a separation chamber, having input and output ports, for separating blood components into components according to their densities. The output port of the separation chamber is in fluid communication with a first container or containers that receive a less-dense component, while the input port is in fluid communication with a second container that receives more-dense components. A phlebotomy needle for withdrawing whole blood from a donor is in fluid communication with a third container containing anticoagulant.

In operation, a collection cycle begins with the withdrawal, through the phlebotomy needle, of whole blood from a donor. The whole blood is anticoagulated by mixing with anticoagulant drawn from the third container, and the anticoagulated whole blood enters the separation chamber through the input port. Lower-density components are separated from higher-density components in the separation chamber. The less-dense component(s) (e.g., plasma and platelets) are displaced through the output port into the first container or containers. The separation process is then terminated, and the higher-density components; (e.g., red blood cells or "RBC") remaining in the separation chamber are diluted with diluent and returned to the donor. More specifically, a diluent solution is stored in a fourth container in selective fluid communication with the flow path between the input port of the separation chamber and the phlebotomy needle, and the higher-density components remaining in the chamber are drawn out through the inlet port, mixed with diluent from the fourth container and returned to the donor via the phlebotomy needle.

In the second part of a collection cycle, whole blood is again drawn from the donor and combined with anticoagulant from the third container. The anticoagulated whole blood enters the separation chamber, which again separates the lower and higher density components. The second separation process is then terminated and the phlebotomy needle is removed from the donor. In this instance the higher-density components remaining in the separation chamber, instead of being returned to the donor, are displaced to a second container which is in selective fluid communication with the input port of the separation chamber. A fifth container containing a volume of additive solution is in fluid communication with the second container and rejuvenates the higher density components entering the second container with additive solution. Since donors can ordinarily part with greater volumes of plasma and platelets than RBC, this process facilitates simultaneous but separate collection of RBC and less-dense components such as plasma or plasma and platelets in proportions tolerable to typical donors.

While efficient and straightforwardly practiced, this approach nonetheless exhibits limitations imposed by the fixed nature of the various apparatus components. In particular, because the volume of the separation chamber cannot be altered, the overall amount of blood components collected during the course of a cycle is constant. If the target collection volume is not an integral multiple of the amount collected in the course of one cycle, procedure time will be increased and blood components needlessly withdrawn from the donor must be returned.

A number of considerations can influence target collection volumes. One key factor is donor physiology. Generally, it is desirable to obtain as much of a blood component as the donor is able to provide without risk of harm. The allowable volume varies from donor to donor, depending on such characteristics as the donor's weight, sex and the concentration of the desired blood component. With current systems, such as the RBC system described in the '187 patent, the operator first manually establishes a target collection volume for one or more blood components from a particular donor, and then computes the number of cycles necessary to obtain that volume. If, as is usually the case, exactly reaching the target collection volume would require a non-integral number of cycles the operator "rounds up" and performs the next higher integral number of cycles, returning to the donor the excess components from the separation chamber and the first collection container. This procedure is cumbersome, wasteful of time and needlessly prolongs the collection process.

DESCRIPTION OF THE INVENTION

Summary of the Invention

The present invention automates the apheresis process to avoid unneeded collection and return of blood components.

In a first aspect, the invention permits an operator to "dial in" a desired amount of one or more blood components (generally RBC, plasma, buffy coat, platelets or some combination), whereupon the invention calculates the number of cycles necessary to achieve the target and directly implements an appropriate apheresis procedure. The calculation of cycles reflects consideration not only of the volume of the separation chamber, but also of donor physiology: different donors may exhibit different concentrations of desired blood components, resulting in varying needed apheresis volumes to achieve a target volume of blood component; and different donors may also exhibit varying depletion tolerances for given blood components. The invention calculates the number of necessary cycles based on characteristics of the donor (as well as the collection efficiency of the apheresis apparatus), and also alerts the operator if the requested target level or the calculated number of cycles exceeds safety guidelines for the particular donor.

In a variation of this aspect, the invention varies the volume of the separation chamber instead of, or in addition to, modifying the number of collection cycles in order to reach a target collection point.

In a second aspect, the invention utilizes a return procedure whereby, prior to the final collection cycle, only a portion of the contents of the separation chamber is returned to the donor. The returned portion is calculated such that filling the partly empty separation chamber on the last collection cycle results in just meeting the collection target.

In a third aspect, the invention dispenses with the need to base target calculations on donor physiology information obtained prior to commencing apheresis. Instead the invention monitors, in real-time, the amount of desired product actually collected during an apheresis cycle, and based thereon calculates the number of cycles necessary to reach the target level. The calculation is preferably adaptive in the sense that monitoring is continuous throughout the procedure, and the number of calculated cycles (including, preferably, partial cycles as discussed above) is continuously adjusted based on the results of ongoing monitoring.

In a fourth aspect, the invention continuously compares overall blood collection volumes with the volume of blood product actually obtained in order to compute (or verify) a machine collection efficiency for each type of blood product collected. This quantity, in turn, is used to estimate the amount of blood that must be drawn in order to obtain a specified amount of a particular blood product.

The invention accordingly includes apheresis apparatus configured to operate in accordance with the foregoing principles, as well as apheresis methods embodying them.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

A. Basic System Design

Figure 1:
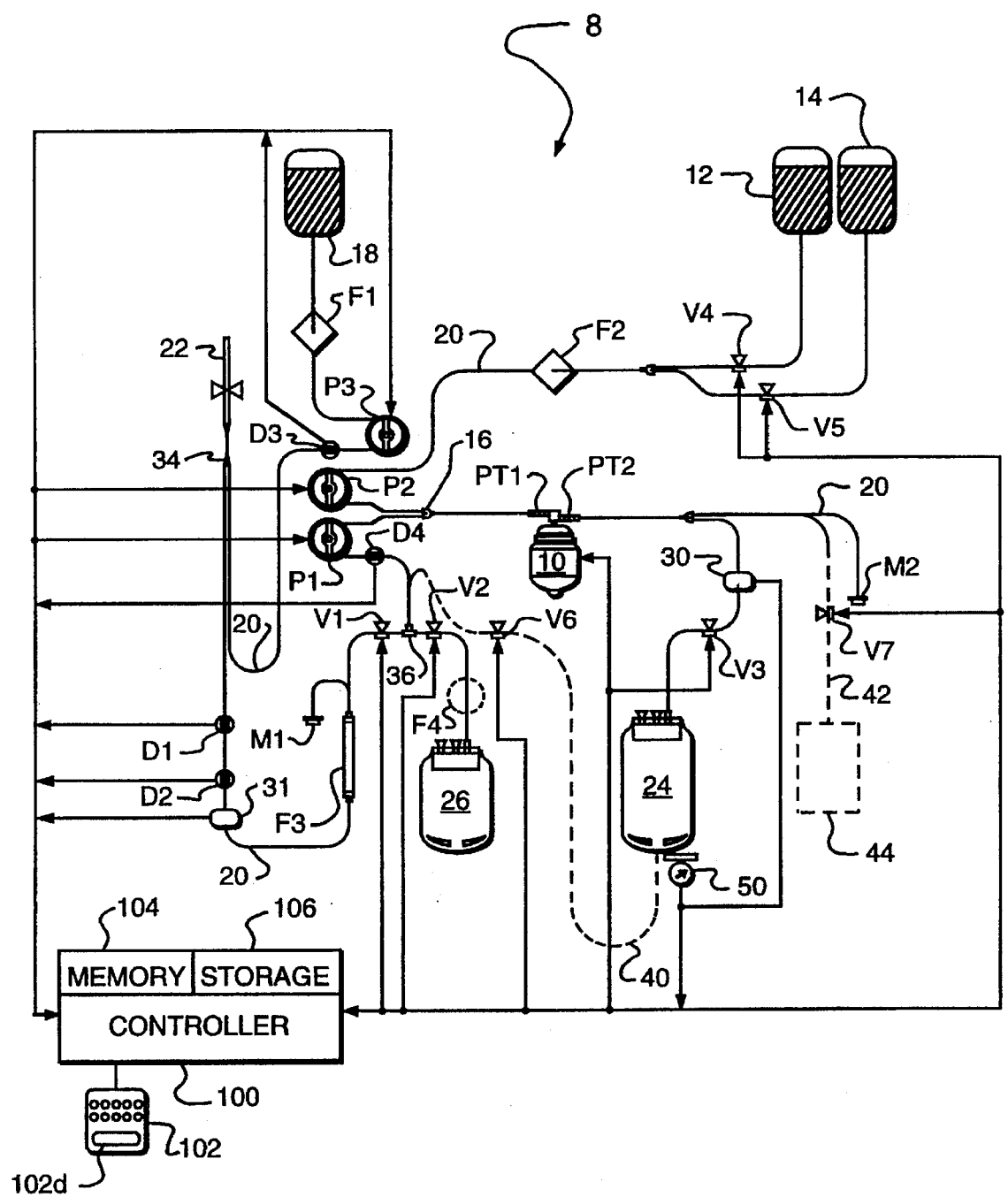
FIG. 1 is a schematic view of an apheresis apparatus embodying the present invention.

Refer first to FIG. 1, which illustrates an apheresis apparatus 8 that utilizes a conventional centrifuge bowl 10 fin accordance, for example, with U.S. Pat. No. 4,983,158) having an internal fluid capacity preferably on the order of 250 ml, means (not shown) for rotating the bowl, an input port PT1 and an output port PT2. Output port PT2 of centrifuge bowl 10 is in fluid communication with a first container 24 for collecting plasma, and input port PT1 is selectively coupled through a series of valves V1, V2, V4 and V5 to a phlebotomy needle 22, a second container 26 for collecting red cells, a fourth container 14 for storing saline solution and a fifth container 12 for storing additive or rejuvenating agent. Phlebotomy needle 22 is in fluid communication with a third container 18 containing anticoagulant. The containers are bags made of blood-compatible material, and the depicted fluid flow path is established by suitable lengths of blood-compatible tubing (denoted collectively by reference numeral 20). The preservation agent is an additive for extending the shelf life of RBC, suitable examples of which include SAGM, ADSOL, NUTRICELL and glycerol.

A pair of bacterial filters F1, F2 remove bacteria from solutions drawn from containers 12, 14 and 18. Three peristaltic pumps P1, P2, P3, together with valves V1, V2, V3, V4, V5 control the direction and duration of flow through blood-compatible tubing 20 in response to signals generated by a controller 100 as described below. Controller 100 monitors the state of the system by means of signals received from a series of sensors and monitors. Specifically, a line sensor 30 monitors the concentration of one or more types of blood cells passing from centrifuge bowl 10 to container 24; another line sensor 31 monitors the concentration of one or more types of blood cells in the whole blood received from the donor; a donor pressure monitor M1 and a system monitor M2 monitor pressure levels within the apparatus 8; and a series of air detectors D1, D2, D3, D4 monitor the presence or absence of fluid within tubing 20. Line sensors 30 can be, for example, arrangements that utilize a light-emitting diode (LED) and a detector positioned on opposite sides of tubing 20, whereby the amount of radiation detected is compared with what the LED actually transmits to determine the turbidity of the fluid passing through tubing 20, the turbidity being indicative of cell concentration. Alternatively, lines sensors 30 can be more elaborate optoelectric components capable of discriminating among differently sized particles, thereby allowing the concentrations of various cell subpopulations (e.g., white blood cells and platelets) to be separately or alternatively determined. Such sensors, as well as suitable pressure monitors and air detectors, are well characterized in the art. Valves V1–V5 are electronically actuable and responsive to open and close signals generated by controller 100.

Operation of the basic system components for collection of RBC is as follows. Controller 100 causes tubing 20 to be primed with saline solution from container 14 by opening valve V2, closing valve V1 and operating pumps P1 and P2. Additionally, controller 100 closes valve V4 and opens valve V5. The pumps draw saline solution through a "Y" connector 16 to air detector D4, which signals controller 100 as soon as the presence of saline solution is sensed; controller 100 thereupon terminates the saline solution priming operation by closing valve V5. (It should be noted that filter F2 can be located in line 20 between pump P2 and connector 16 to facilitate higher flow rates.) Next, controller 100 operates pumps P1 and P3 to prime the tubing 20 and needle 22 with anticoagulant solution from container 18. The anticoagulant passes through a "Y" connector 34 and continues to air detector D2, which signals controller 100 as soon as the presence of anticoagulant is sensed; controller 100 thereupon terminates the anticoagulant priming operation.

Next, controller 100 operates pump P1 to draw the anticoagulant closer to a filter F3 through tubing 20 to equalize any pressure created within apparatus 8, thereby preventing anticoagulant from being injected into the donor when phlebotomy needle 22 is inserted. In performing this operation, controller 100 utilizes signals indicative of line pressure received from pressure monitor M1 and system monitor M2, terminating the equalizing operation once the pressure at M1 substantially matches that at M2. The phlebotomy needle 22 is then inserted within the donor, and controller 100 causes whole blood to be drawn from and mixed with anticoagulant by operating pumps P1 and P3, pump P3 mixing anticoagulant from container 18 with the drawn whole blood drawn so as to maintain a target ratio (generally 1:16) of anticoagulant to whole blood. Valves V1 and V3 are open, forcing anticoagulated whole blood into bowl 10 through input port PT1.

Controller 100 then initiates rotation of bowl 10, and centrifugal forces separate the higher density components (mainly RBC), from lower density components (white blood cells, platelets and plasma). In particular, rotation of the centrifuge bowl concentrates RBC cells against the outer bowl wall. With continued ingress of blood the supernatant, comprising lighter blood components, anticoagulant and debris, forms concentric layers that approach the core of the bowl and exit out the outlet port PT2. The plasma passes through line sensor 30 and valve V3 before being collected in plasma container 24, which holds approximately 400-600 ml of plasma. When nearly all separated plasma has been sent to container 24 (as indicated, for example, by increasing turbidity detected by line sensor 30, or a weight gauge 50 whose output is coupled to controller 100), the separation process is terminated by stopping the rotation of the centrifuge. Controller 100 causes pump P1 to return the blood components remaining in bowl 10 to the donor through filter F3 and phlebotomy needle 22 with valve V1 open and valve V2 closed. Simultaneously, controller 100 operates pump P2 to mix saline solution from container 14 with the blood components being returned to the donor (the addition of saline reduces the citrate effect experienced by the donor); valve V5 is kept open and valve V4 closed. The components are preferably returned to the donor at a rapid rate, e.g., 120 ml/min. At that return rate, the saline solution is introduced by pump P2 at a rate of approximately 60 ml/min. Alternatively, the contents of the bowl can be diluted and returned with a portion of the donor's plasma from container 24. While the contents of the bowl 10 are being returned to the donor, controller 100 causes pump P2 to prime apparatus 8 with additive solution stored in container 12 up to "Y" connector 16 with valve V4 open and valve V5 closed.

Apparatus 8 then begins a second draw process in which whole blood is again obtained from the donor and mixed with anticoagulant. Another 200-250 ml of plasma is separated in bowl 10 and displaced through output port PT2 into plasma container 24. The second centrifugation process is then terminated (again, by signals provided by line sensor 30 or weight gauge 50), and the phlebotomy needle 22 removed from the donor. Controller 100 operates pump P1 to drive the higher-density components remaining in bowl 10 out through port PT1. These components are rejuvenated with an additive solution drawn from container 12 by pump P2 with valve V4 open and valve V5 closed. Optionally, the rejuvenated components can be filtered through a leukocyte filter F4 before being collected in red cell container 26 with valve V1 closed and valve V2 open. Filter F4 filters out white blood cells from the diluted components and is then purged, completing the procedure. Alternatively, the contents of the bowl can be collected in container 26 before the additive solution is added; in this case, filter F4 is omitted. In a further alternative, additive solution can be preloaded in container 26; in this case, additive container 12 is omitted.

In other alternative embodiments, additional collection containers can be added to apparatus 8 in fluid communication with output port PT2 for the collection of platelets and white blood cells. Furthermore, bowl 10 can alternatively be a Latham-type bowl. In order to collect platelets and/or white blood cells, a surge line 40 (shown in dotted lines) and a valve V6 are added between plasma container 24 and valve V2. A platelet container 44, a line 42 and a valve V7 are also added. Surge line 40 allows plasma to recirculate through bowl 10, assisting the collection of platelets in container 44 as disclosed in U.S. Pat. Nos. 4,416,654 and 4,464,167.

The novel functions of the present invention are implemented on the foregoing basic platform through suitable configuration of controller 100, as described below. Controller 100 may itself be implemented, for example, using a programmable, single-chip microcomputer which incorporates analog-to-digital converters for transforming the signals from the various analog sensors into digital signals that may be processed by the microcomputer. Alternatively, the circuitry may be implemented in a custom integrated circuit or in discrete electronics. Controller 100 also includes a keypad 102 or other input/output device for receiving data from an operator.

It should be emphasized that the present invention is not limited to apparatus configured for collection of any one type of blood component, and the foregoing configuration is intended as exemplary. The control aspects of the invention are usefully practiced in conjunction with virtually any type of blood-separation and collection system, regardless of the ultimate product or products obtained. For example, as noted above, the apparatus described earlier can be used (or straightforwardly modified) to carry out a variety of different procedures, each with the aim of harvesting a different blood component. In a preferred approach, controller 100 includes a computer memory 104 that stores procedural steps implementing a blood-processing routine, or "protocol," selected by an operator; and a permanent storage device 106, such as a hard disk or a CD-ROM drive, which stores a plurality of protocols, any one of which can be loaded into memory 104 for execution. The functioning of apparatus 8 and the blood component ultimately harvested is then determined by the selected protocol in memory 104.

For example, three exemplary protocols that lend themselves to automation are the RBC and plasma procedure discussed above, the "RBC and platelets" protocol, the "single-donor platelets" (SDP) protocol and the "platelets and plasma" (PLP) protocol. In the SDP protocol, a platelet concentrate is collected from an individual donor in one procedure. Blood is drawn from the donor and passed through a centrifuge bowl, which separates the blood into red cell, white cell, platelet and plasma components. The platelet fraction is collected, ordinarily in a removable, sterile blood bag, until a desired yield is obtained; the remaining fractions are returned to the donor. In the PLP protocol, both platelet and plasma fractions are retained, ordinarily in separate containers. Specific parameters and operating procedures to effectuate these protocols are well-known to those skilled in the art. Other apheresis protocols (e.g., harvesting of fresh plasma; therapeutic plasma exchange, in which a patient's plasma is replaced with plasma from a healthy donor; and mononuclear cell collection, in which white cells are collected) are also well-characterized in the art.

Figure 2:
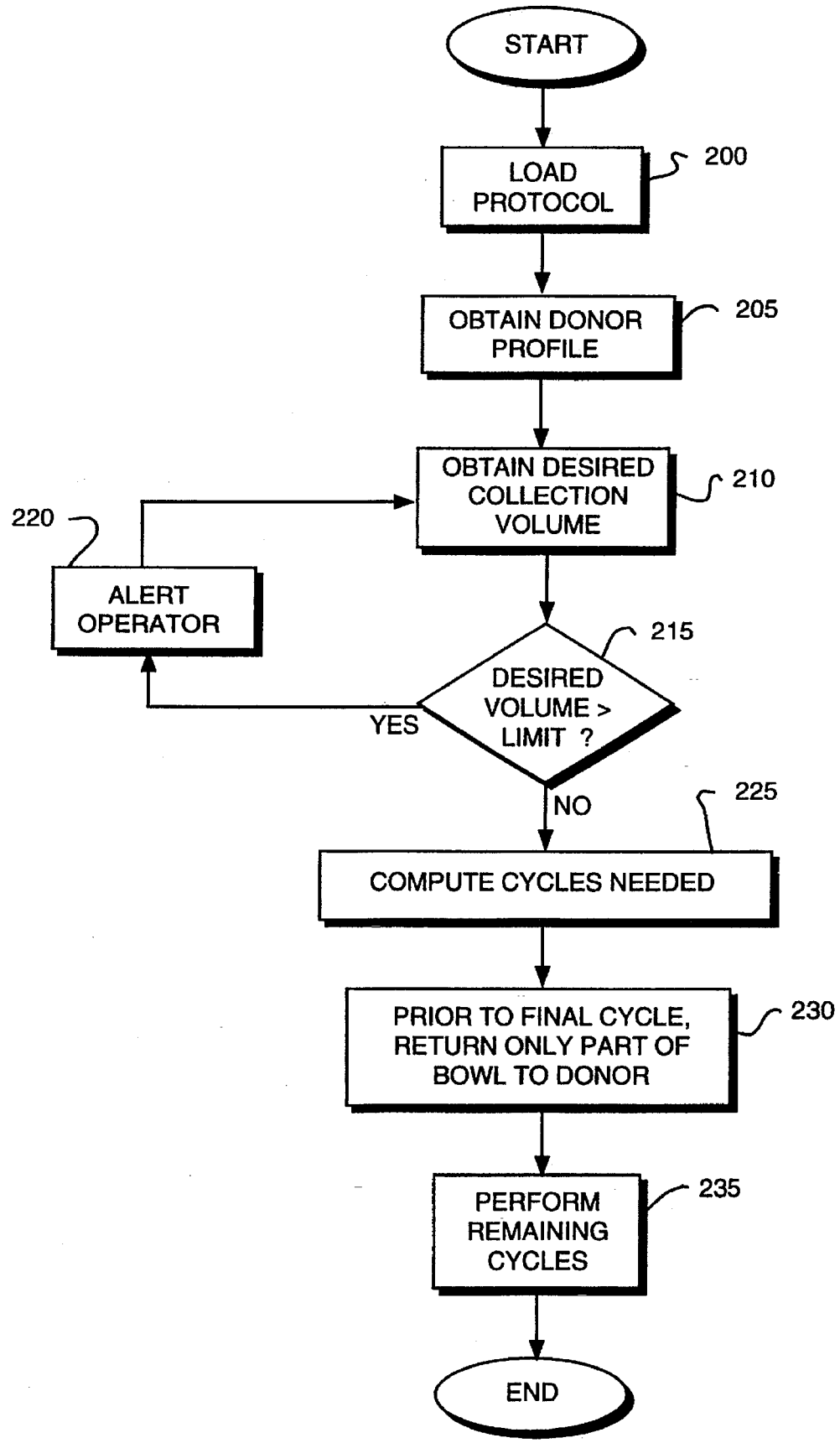
FIG. 2 is a flow chart illustrating the donor safety, cycle calculation and partial return features of the present invention.

Using this approach, controller 100 implements the procedural steps for obtaining RBC and plasma using stored instructions encoding the following steps:

1. Prime with saline (open V2, V4; close V1, V5; operate P1, P2)
2. Prime with anticoagulant (close V4; operate P1, P3)
3. Equalize pressure
4. Draw blood (open V1, V3; operate P1, P3)
5. Rotate bowl until collection complete
6. Stop rotation
7. Return bowl contents to donor (open V1, V4; close V2, V5; operate P1, P2)
8. Prime with additive (close V4; open V5; operate P2)
9. Draw blood (open V1, V3; operate P1, P3)
10. Rotate bowl until collection complete
11. Rejuvenate (close V4; open V5; operate P2)
12. Stop rotation B. Automatic Cycle Determination Using keypad 102, the operator selects a desired protocol, keys in a desired collection volume, and enters physiological information for the donor. Controller 100 thereupon executes the procedural steps shown in FIG. 2 to automatically collect the entered amount of blood component, preferably without excess collection and return of blood.

In a first step 200, controller 100 loads the instructions corresponding to the selected protocol into memory 104 from storage device 106. The protocol includes safety guidelines placing an upper limit on the allowable collection volume based on the donor's profile; in particular, the protocol includes one or more mathematical formulas operating on selected donor physiological characteristics to produce the upper collection limit. Alternatively, the protocol can include tabular data, the upper limit being obtained by table lookup. Typically, the donor profile information includes sex, weight and an approximate concentration, in the donor's blood, of the desired blood component; the latter quantity is usually obtained in a "pre-count" analysis of a small amount of the donor's blood. For example, a normal adult male has approximately 75 mL of blood for each kg of body mass, and an average whole-blood hematocrit of 0.41; accordingly, the volume of RBC in mL for a typical adult male donor is given by (body mass)(75)(0.41). A safely allowable collection fraction of this volume is 22.5%. For RBC collection, the collection efficiency of the apheresis apparatus described above approaches 100%.

In step 205, controller 100 prompts the operator, via a display 102d on keypad 102, to enter the necessary donor physiological information. This is stored in memory 104 and processed in accordance with the information contained in the protocol to obtain an upper collection limit. Preferably, this limit is displayed to the operator.

In step 210, the operator enters the desired blood-component collection volume using keypad 102. If this volume exceeds the upper limit (step 215), controller 100 alerts the operator (step 220) using, e.g., the display 102d of keypad 102. The operator is then invited to enter a different value.

In step 225, controller 100 computes the number of cycles necessary to achieve the desired collection volume. This quantity is straightforwardly obtained based on the amount of blood processed during each cycle (which itself depends largely on the volume of the centrifuge bowl) and the collection efficiency of the apheresis apparatus for the particular blood component. The number of cycles typically will not be integral; although it is possible simply to "round up" in accord with the prior art, collecting too much blood and returning the excess to the donor, preferably the invention is utilized in a manner that avoids this wasteful practice. Specifically, prior to the final collection cycle, only a portion of the bowl contents is returned to the donor. The returned portion is calculated such that filling the partly empty bowl during the last collection cycle results in just meeting the collection target.

This partial-return strategy is illustrated at steps 230, 235. The mantissa or decimal portion of the number of calculated collection cycles is utilized to determine the portion of the bowl contents retained during the bowl-emptying step of the penultimate collection cycle. In particular, the retained proportion is equal to one minus the mantissa value. Then, with the bowl partly filled, the final collection cycle is executed normally, collection terminating when the bowl becomes full. The contents of the full bowl are then utilized in the normal fashion (transferred to a storage container, in the case of RBC harvesting; or returned to the donor, in the case of platelet or plasma collection).

For example, in the case of the RBC and plasma collection protocol described above suppose that the plasma contained in 2.6 bowl volumes is desired. Each full cycle fills the bowl twice. During the return phase of the second collection cycle, instead of returning the entire bowl to the donor, only 60% is returned (leaving 0.4 bowl volume remaining). The bowl is then filled and fully emptied during the second pass of the cycle, resulting in a total of 1.6 bowl volumes during the second collection cycle and 2.6 bowl volumes overall.

C. Variation of Bowl Volume

As noted previously, the fixed volume of the separation chamber results in a constant per-cycle collection amount. Instead of (or in addition to) varying the number of cycles, it is possible to utilize a separation chamber whose design permits alteration of the interior volume. An example of such a design is described in U.S. Pat. No. 3,737,096 (the entire disclosure of which is hereby incorporated by reference), which contemplates a centrifuge having a flexible interior membrane that may be selectively filled with hydraulic fluid from an exterior source. Entry of hydraulic fluid into the membrane expands its volume, thereby reducing the interior volume of the centrifuge.

Figure 4:
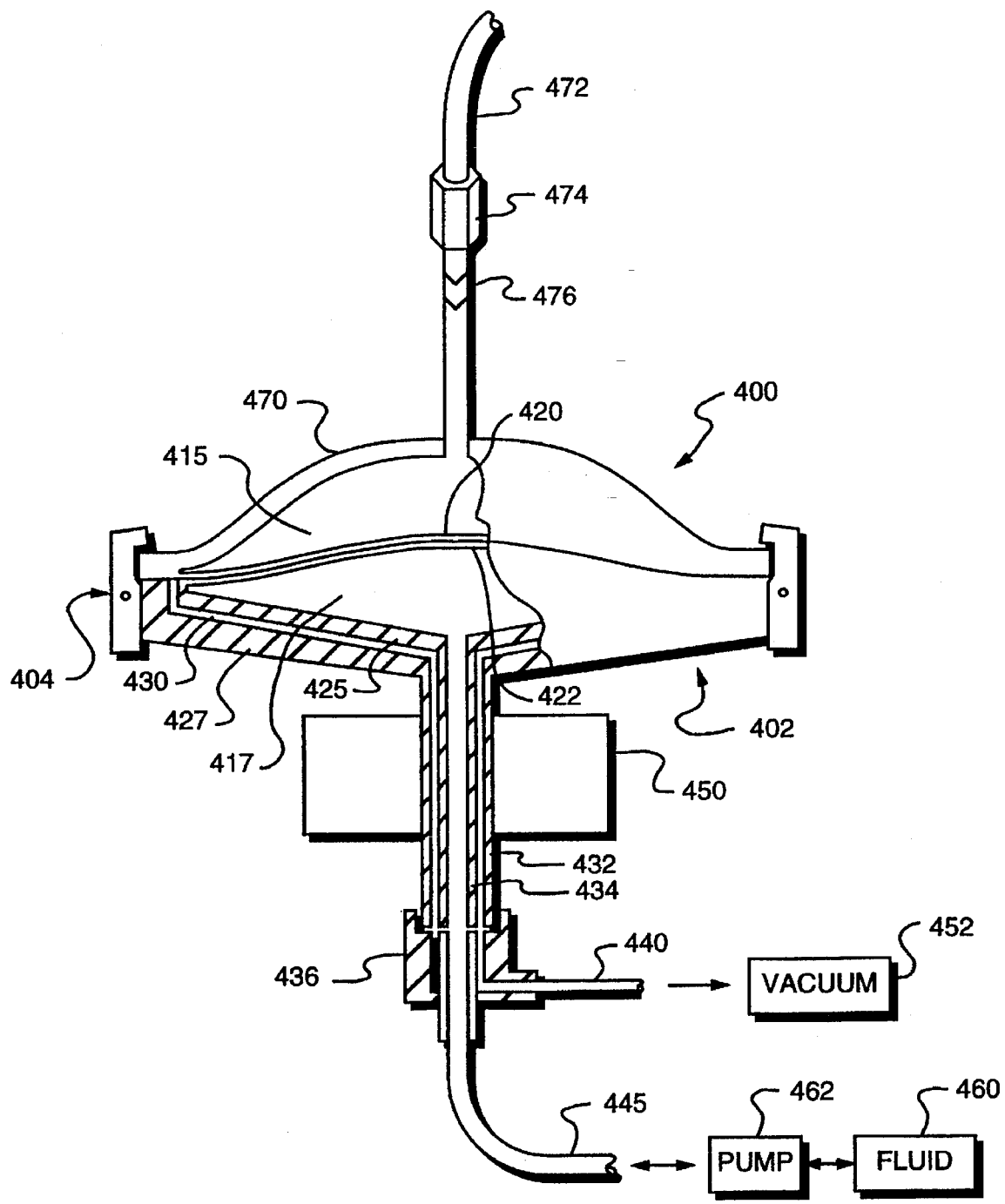
FIG. 4 is a partial-cutaway view of a variable-volume separation chamber used in the context of the present invention to avoid partial cycles.

Refer to FIG. 4, which illustrates application of this concept to the environment of the present invention. The illustrated design is divided into a disposable member 400 and a permanent member 402, which are held together during operation by a chuck 404. The combined device comprises a blood centrifuge having two interior compartments 415, 417 defined by flexible membranes 420, 422 that are substantially in contact with one another. To maintain this condition, a vacuum is continuously applied to the interface region between them. In permanent member 402, membrane 422 is joined to a rigid inner shell 425, which overlies a rigid outer shell 427. The two shells are joined (e.g., by spaced-apart posts) so as to preserve an interior space 430 between them. This space defines a fluid path that is preserved as shells 425, 427 narrow to define a pair concentric cylindrical members 432, 434. A rotary seal 436 couples interior space 430 to a vacuum line 440, and compartment 417 to a volume-control line 445, so as to maintain continuous, closed fluid pathways through the lines as the joined assemblies 400, 402 are rotated by a centrifuge motor 450. The vacuum that retains membranes 420, 422 in contact is maintained through vacuum line 440 by a vacuum pump 452, which contains a sensor to continuously monitor the pressure within space 430.

Compartment 417 is filled with a variable amount of a hydraulic fluid 460 by means of a volumetric pump 462, which can force or withdraw fluid into or from compartment 417 through control line 445. The volume of compartment 417 determines the available interior volume of compartment 415, and therefore the amount of collected blood that can be retained therein. A pressure sensor associated with pump 462 and coupled to controller 100 detects the pressure within compartment 417, which corresponds to the amount of fluid in compartment 417 and therefore its volume, allowing controller 100 direct control over that volume through operation of pump 462.

Disposable member 400 comprises a rigid exterior shell 470 (fabricated, like shells 425, 427, from a stiff, durable material such as hard plastic), which is joined to membrane 420. Blood enters and exits compartment 415 through a tubing line 472, which penetrates shell 470 through a one-way rotary seal 474. If compartment 415 is to contain a fluid, such as anticoagulant, it may be desirable to add a breakable seal 476 to isolate the contents of compartment 415 until use.

Based on the machine collection efficiency and the desired amount of blood product entered by the operator, controller 100 determines an overall amount of blood that must be processed in order to meet the target. Because the processing volume of centrifuge 410 is variable, however, controller 100 next computes whether, first, the volume can be expanded (by withdrawal of hydraulic fluid from volume 417) to the point where the target can be reached with a single complete fill of volume 415. If so, controller 100 obtains the necessary volume it has computed by causing pump 432 to withdraw the appropriate amount of fluid from volume 417, and proceeds with the collection cycle as described above. If, on the other hand, more than one cycle is necessary, controller 100 computes the centrifuge volume corresponding to the smallest integral number of cycles necessary to achieve the target. For example, if 2.4 chamber volumes must be processed, controller 100 causes hydraulic fluid to enter volume 417 until volume 415 is equivalent to 80% of a full volume, and initiates three collection cycles at this volume.

D. Adaptive Control

Figure 3:
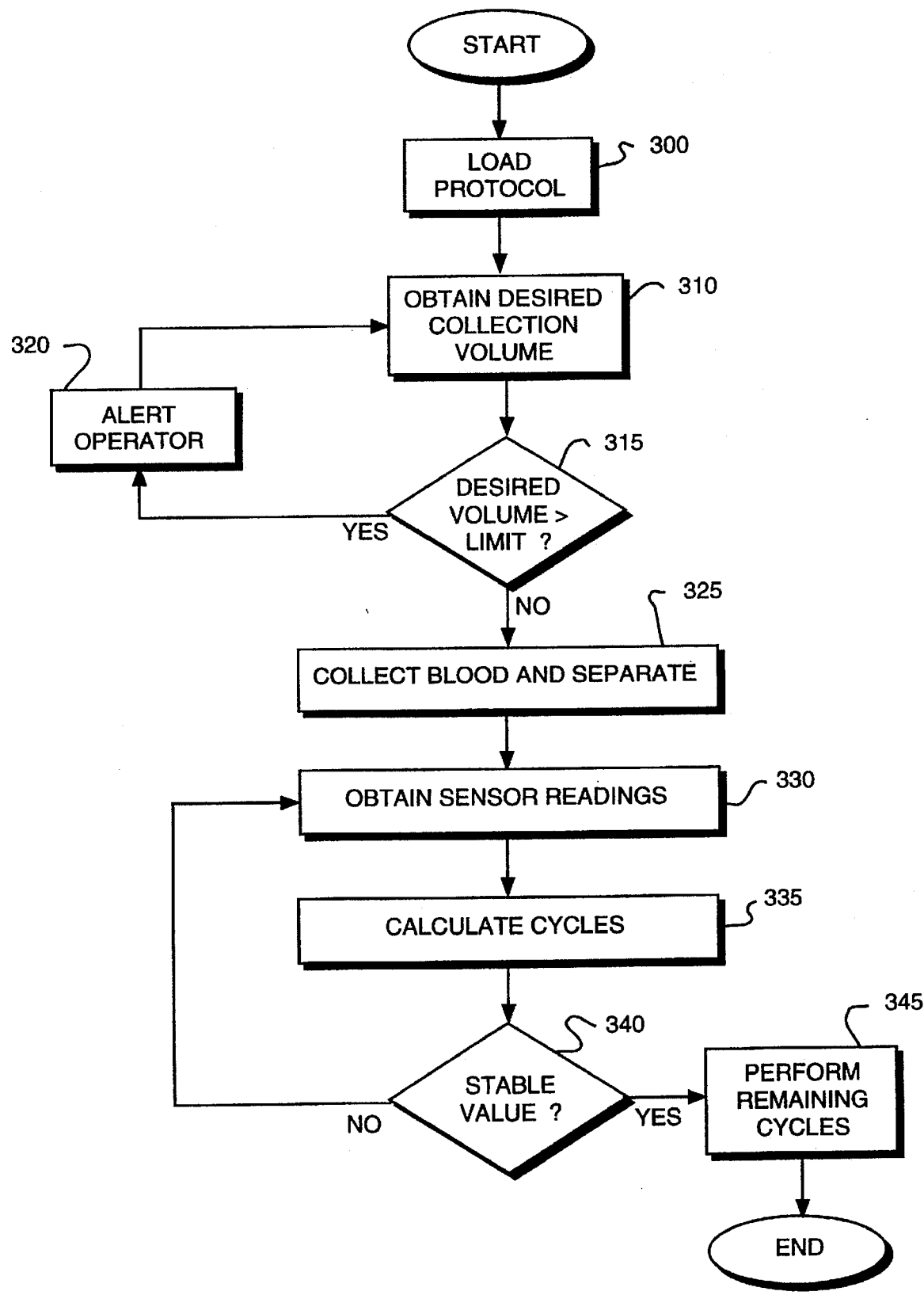
FIG. 3 is a flow chart illustrating the adaptive cycling feature of the present invention.

The manner in which the invention can be configured to perform adaptive cycling, in which observed blood composition (rather than manually entered donor-profile information) is used to determine the number of collection cycles necessary to obtain a target amount of blood component, appears in FIG. 3. The steps of loading a protocol, obtaining a desired collection volume and determining whether this volume exceeds some absolute limit are the same as discussed above. (Although it will be necessary to enter at least some donor information such as sex and weight if this safety check is to be performed, the need to analyze the donor's blood prior to apheresis in order to obtain a "pre-count" is eliminated.)

In step 325, the apheresis apparatus is operated, and blood collected and separated, in accordance with the selected protocol. As separation begins, line sensors measure the concentration of the desired blood component in the whole blood and/or in a branch of tubing 20 that contains a more isolated fraction of the desired blood component (step 330); the sensors transmit concentration information to controller 100, which utilizes the information in calculating the necessary number of cycles (step 335). Because it is possible for the concentration of a particular blood component to vary over the course of one or more collection cycles, the invention provides for periodic update calculations obtained over time during collection, and which are compared with earlier calculations. The invention treats the calculated number of cycles as final only when the variation between calculations falls below a minimum value (e.g., 5%). Thus, in step 340, the results of the current calculation are compared with the previous calculation or with an average based on a plurality of previous calculations, and the process repeated if the variation is too great. When a stable calculated value is obtained, the apparatus performs the remaining number of calculated cycles (step 345). Preferably, the series of cycles is completed using the partial-return strategy set forth above.

The particular sensors that are utilized in monitoring blood-component concentration and their locations within the apparatus depend on the blood component itself. In the case of RBC, for example, line sensor 31 can be used to sense RBC concentration (hematocrit) by measuring absorption, through flowing blood, of light that is characteristically absorbed by RBC but not by free hemoglobin or other blood components. Red light of wavelength 670 nm is suitable for this purpose. A suitable arrangement is described in U.S. Pat. No. 5,385,539 (the entire disclosure of which is hereby incorporated by reference).

The concentration of blood components such as platelets, which are not easily distinguished in whole blood, can be measured by line sensor 30, which is located upstream of the separation chamber and therefore can operate on blood fractions rich in platelets. Thus, the output of sensor 30 is continuously provided to controller 100 and indicates the turbidity of fluid passing through the detector. The turbidity level increases as the platelet-rich fraction follows the plasma fraction out the bowl. When the turbidity reaches the range characteristic of the platelet-rich fraction, the level can be used to estimate the platelet concentration.

The plasma concentration can be estimated using line sensor 31 to derive a hematocrit level, or using weight gauge 50. In the latter case, the rate at which plasma fills container 24 is measured against the overall blood-withdrawal rate.

Because the collection efficiency of a particular apheresis apparatus can vary from donor to donor, it may be preferable to continually recompute the machine collection efficiency ("MCE") over time in order to more accurately compute necessary blood collection volumes. The invention can be configured to compare, for each collection cycle, the amount of blood product actually collected with the amount expected, and to obtain therefrom an actual MCE. This value, in turn, can be compared with a previous or default MCE value and used to obtain a more accurate value, which can be used in the next cycle.

Figure 5:
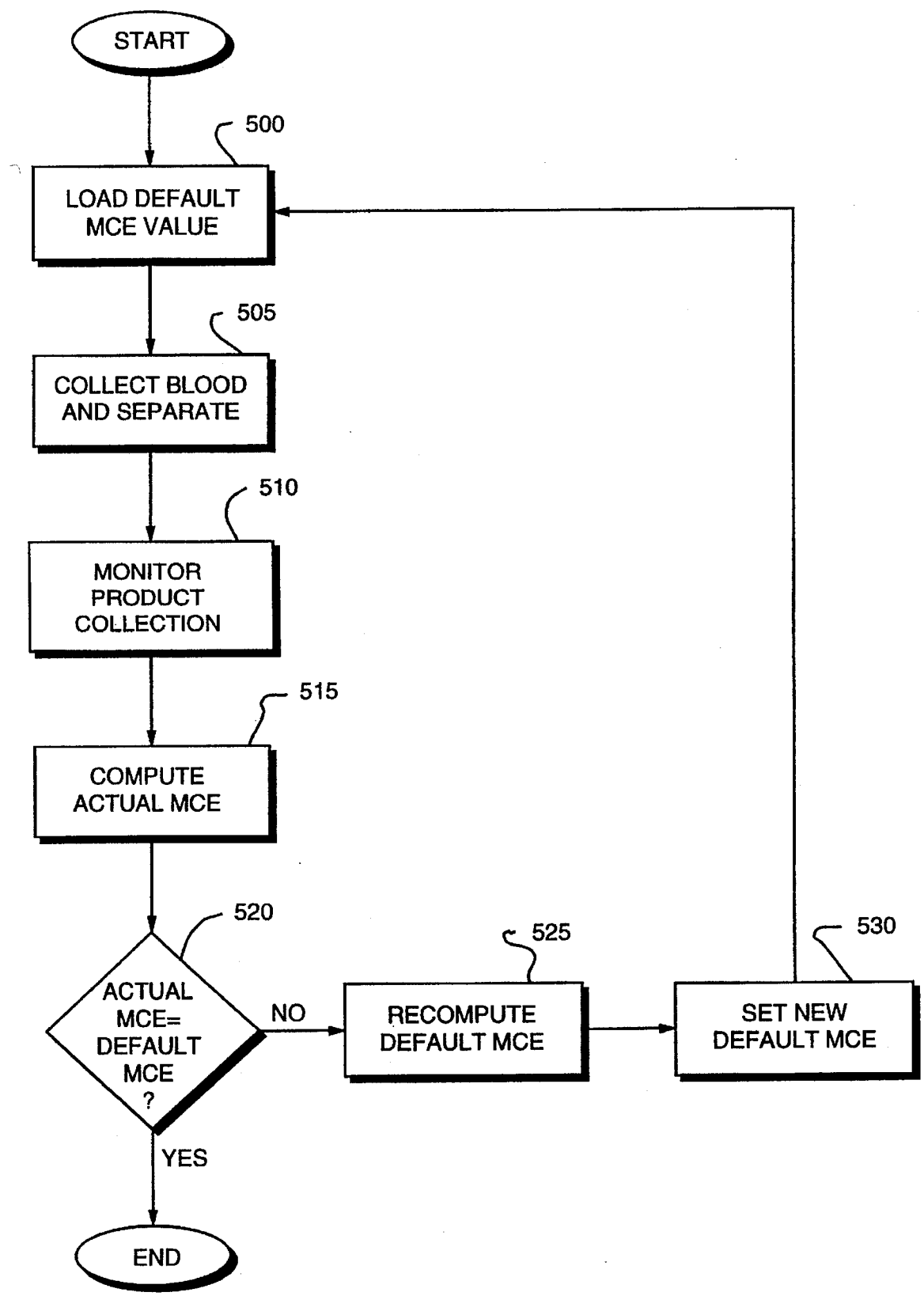
FIG. 5 is a flow chart illustrating iterative computation of the machine collection efficiency.

This process is illustrated in FIG. 5. In a first step 500, preparatory to blood collection and processing, a default MCE value is loaded into memory 104, and a provisional number of cycles necessary to collect the operator-entered target collection amount is computed therefrom. The amount of blood product actually collected is determined in step 510 (e.g., using weight gauge 50 or a line sensor), and, based on this value and the amount of blood drawn from the donor, the invention computes a true MCE value at step 515. The invention then compares this value to the default value loaded in step 500 (step 520). If the computed MCE value matches the default value within some user-specified or machine-specified tolerance, the default value is left unmodified.

If, however, the actual MCE differs from the default MCE, the default MCE is recomputed at step 525. Preferably, the actual MCE is averaged with the then-existing MCE; the averaging can be a straight mean, or can instead be weighted to account for the number of previous computations. In the later case, no single MCE will have any greater effect on the recomputed default value than any other MCE.

In step 530, the default MCE utilized at step 500 is replaced with the recomputed default MCE, and the entire process can repeat for another cycle. Preferably, at step 505, the number of necessary cycles is recomputed based on the new MCE value.

It will therefore be seen that the foregoing represents a convenient, safe and effective approach to blood apheresis. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. Apheresis apparatus comprising:
   a. means for withdrawing blood from a donor, said means comprising a phlebotomy needle and a pump;
   b. means for separating the withdrawn blood into a plurality of components;
   c. means for obtaining the concentration, in the donor's blood, of a selected cellular blood component;
   d. control means, coupled to the withdrawal and separating means, for collecting a predetermined amount of the selected blood component based on the obtained concentration, the control means operating the withdrawing means and the separating means in cycles each comprising:
      i. operation of the pump to withdraw, through the phlebotomy needle, an amount of blood from the donor and provision thereof to the separating means, which separates the withdrawn blood into the plurality of components, the amount of blood being sufficient to fill the separating means;
      ii. collection, from the separating means, of the selected blood component; and
      iii. return of blood components remaining in the separating means to the donor, the apparatus exhibiting, for the selected blood component, a collection efficiency factor specifying a collectable quantity of the selected blood component per unit volume of blood, the control means being configured to calculate, based on the collection efficiency factor, the obtained concentration and the amount of blood collected during a cycle, the number of cycles needed to collect the predetermined amount of the selected blood component.

2. The apparatus of claim 1 wherein the means for obtaining the concentration comprises at least one line sensor coupled to the control means, the apparatus exhibiting, for the selected blood component, a collection efficiency factor specifying a collectable percentage of the selected blood component given the concentration, the control means being configured to calculate, based on the collection efficiency factor and the amount of blood collected during a cycle, the number of cycles needed to collect the predetermined amount of the selected blood component.

3. The apparatus of claim 2 wherein the control means calculates the number of cycles based on a plurality of time-separated concentration measurements.

4. The apparatus of claim 1 wherein the means for obtaining the concentration comprises means for acquiring data entered by a user.

5. The apparatus of claim 1 wherein the selected blood component is chosen from the group consisting of red blood cells, buffy coat and platelets.

6. The apparatus of claim 1 further comprising:
   a. input means for obtaining information from an operator, the information including an amount of a selected blood component and at least one donor physiological characteristic;
   b. output means for reporting information;
wherein
   c. the control means is coupled to the withdrawal means, the separating means, the input means and the output means and is configured to:
      i. calculate, from the at least one physiological characteristic, a maximum amount of the blood component that may be safely collected from the donor;
      ii. compare the calculated amount with the operator-entered amount;
      iii. provide an alert signal, over the output means, if the calculated amount exceeds the operator-entered amount; and
      iv. if the calculated amount does not exceed the operator-entered amount, operate the withdrawing means and the separating means to separate, from withdrawn blood, the operator-entered amount of the selected blood component.

7. The apparatus of claim 6 wherein the at least one donor physiological characteristic comprises weight and sex.

8. The apparatus of claim 6 further comprising at least one collection container for collecting the at least one blood component.

9. The apparatus of claim 1 further comprising means for recomputing the collection efficiency factor after each cycle.

10. Apheresis apparatus comprising:
    a. means for withdrawing blood from a donor, said means comprising a phlebotomy needle and a pump;
    b. means for separating the withdrawn blood into a plurality of components;
    c. means for obtaining the concentration, in the donor's blood, of a selected blood component;
    d. input means for obtaining, from an operator, a desired amount of the selected blood component; and
    e. control means, coupled to the withdrawal and separating means, for collecting a predetermined amount of the selected blood component based on the obtained concentration, the control means operating the withdrawing means and the separating means in cycles each comprising:
       i. operation of the pump to withdraw, through the phlebotomy needle, an amount of blood from the donor and provision thereof to the separating means, which separates the withdrawn blood into the plurality of components, the amount of blood being sufficient to fill the separating means;

ii. collection, from the separating means, of the selected blood component; and iii. return of blood components remaining in the separating means to the donor, the apparatus exhibiting, for the selected blood component, a collection efficiency factor specifying a collectable percentage of the selected blood component, the control means being configured to calculate, based on the collection efficiency factor, the obtained concentration and the amount of blood collected during a cycle, the number of cycles needed to collect the predetermined amount of the selected blood component, and the apparatus being further configured to collect operator-entered amounts of the selected blood component corresponding to non-integral numbers of cycles, each non-integral number including a mantissa portion, by (i) in a penultimate cycle, during return of blood components remaining in the separating means to the donor, retaining in the separating means a fraction of the remaining blood components equal to the mantissa, and (ii) in a final cycle, during withdrawal of blood from the donor, withdrawing only enough blood to fill the separating means.

11. The apparatus of claim 10 wherein the blood component is platelets.

12. The apparatus of claim 10 wherein the blood component is red blood cells.

13. The apparatus of claim 10 wherein the blood component is buffy coat.

14. The apparatus of claim 10 wherein the blood component is plasma.

15. Apheresis apparatus comprising:

a. means for withdrawing blood from a donor, said means comprising a phlebotomy needle and a pump;

b. variable-volume separation means for separating the withdrawn blood into a plurality of components, the separating means having a volume;

c. means for obtaining the concentration, in the donor's blood, of a selected blood component;

d. control means, coupled to the withdrawal means and the separating means for collecting a predetermined amount of the selected blood component based on the obtained concentration, the control means operating the withdrawing means and the separating means in cycles each comprising:

i. operation of the pump to withdraw, through the phlebotomy needle, an amount of blood from the donor and provision thereof to the separating means, which separates the withdrawn blood into the plurality of components, the amount of blood being sufficient to fill the separating means;

ii. collection, from the separating means, of the selected blood component in the collection container; and iii. return of blood components remaining in the separating means to the donor, the control means also determining, based on the concentration of the selected blood component and the predetermined amount thereof an optimal separation-chamber volume and causing the separation chamber to assume the optimal volume.

16. The apparatus of claim 15 wherein the apparatus exhibits, for the selected blood component, a collection efficiency factor specifying a collectable quantity of the selected blood component per unit volume of blood, the control means calculating the optimal volume based on the collection efficiency factor and the obtained concentration.

17. The apparatus of claim 16 wherein the optimal volume facilitates collection of the predetermined amount of the selected blood component in an integral number of cycles and without variation of the volume.

18. The apparatus of claim 15 further comprising means for recomputing the machine collection efficiency after each cycle.

* * * * *